(12) United States Patent
Behnam

(10) Patent No.: US 7,208,594 B2
(45) Date of Patent: Apr. 24, 2007

(54) ISOFLAVONE CONCENTRATES AS WELL AS METHODS FOR THEIR PRODUCTION

(75) Inventor: Dariush Behnam, Rossdorf (DE)

(73) Assignee: Aquanova AG, Darmstadt (DE)

( * ) Notice: Subject to any disclaimer, the term of this patent is extended or adjusted under 35 U.S.C. 154(b) by 216 days.

(21) Appl. No.: 10/450,539

(22) PCT Filed: Jun. 29, 2002

(86) PCT No.: PCT/EP02/07194
§ 371 (c)(1),
(2), (4) Date: Jun. 23, 2003

(87) PCT Pub. No.: WO2004/002469

PCT Pub. Date: Jan. 8, 2004

(65) Prior Publication Data

US 2004/0220116 A1   Nov. 4, 2004

(51) Int. Cl.
*A61K 31/7048* (2006.01)
*A01N 65/00* (2006.01)

(52) U.S. Cl. .......................... 536/128; 536/8; 536/124; 536/127; 424/757; 514/2; 514/27; 514/456; 514/455; 426/634; 435/68.1

(58) Field of Classification Search ................ 536/128, 536/8, 124, 127; 424/757; 514/2, 27, 456, 514/455, 783, 25, 26; 426/634; 530/378; 435/68.1

See application file for complete search history.

(56) References Cited

U.S. PATENT DOCUMENTS

| 5,824,702 | A | | 10/1998 | Wei | |
|---|---|---|---|---|---|
| 6,096,343 | A | * | 8/2000 | Gergely et al. | 424/499 |
| 6,261,565 | B1 | * | 7/2001 | Empie et al. | 424/757 |
| 6,300,377 | B1 | * | 10/2001 | Chopra | 514/715 |
| 6,495,718 | B1 | | 12/2002 | Schmidt | |

FOREIGN PATENT DOCUMENTS

| DE | 101 04 847 A | | 12/2001 |
|---|---|---|---|
| DE | 101 03 454 A | | 8/2002 |
| EP | 0 385 445 A | | 9/1990 |
| EP | 1 055 408 A1 | | 5/2000 |
| WO | WO 99/38509 | * | 5/1999 |
| WO | WO 99 38509 A | | 8/1999 |
| WO | WO 02 085328 | | 10/2002 |

\* cited by examiner

*Primary Examiner*—Shaojia Anna Jiang
*Assistant Examiner*—Devesh Khare
(74) *Attorney, Agent, or Firm*—Jacobson Holman PLLC

(57) ABSTRACT

Isoflavone concentrates are described, which contain at least about ten to about twenty weight parts of polysorbate to one weight part of isoflavone containing a genistein, and/or daidcein, and/or glycitein. Further, a method for the production of an isoflavone concentrate is described.

14 Claims, 1 Drawing Sheet

ISOFLAVONE CONCENTRATES AS WELL AS METHODS FOR THEIR PRODUCTION

This is a nationalization of PCT/EP02/07194 filed Jun. 29, 2002 and published in German.

The invention relates to isoflavone concentrates, as well as to a method for their production.

Hormones are chemical compounds that are synthesized in special organs or cells, and are then transported to a different location in order to coordinate growth, development, and physiological-metabolical performances at a very low concentration.

Plants contain compounds that have no hormonal character for the same, which produce hormone-similar effects in the mammal, however. The one known best are the so-called isoflavones from legumes. For instance, soy contains genistein, isogenistein, and formononetine. These agents have estrogen effects, and therefore have a very positive influence on post-menopausal symptoms, such as problems with blood circulation, type II diabetes, and osteoporosis, fortunately without any side effects. In this way, they indirectly influence the mortality rate. General ageing phenomena, such as of the skin, are also part of this circle of protective qualities. For decades the average isoflavone absorption in Asia has been between 20 and 100 mg/day; it is much less than that in Western countries.

Isoflavones of the type genistein are contained in soy, and in many other plants. Nutrition based on soy, which is common mainly in Asia, is attributed to the fact that much less carcinomas (breast, prostate, skin) occur there, and that post-menopausal symptoms in women occur rarely. Isoflavones are so-called phytoestrogens, and bind to the estradiol receptor. With animal tests and skin models, it was found that these isoflavones increase the intracellular, enzymatic, antioxydative potential. This is in part due to its effect.

Figure 1:
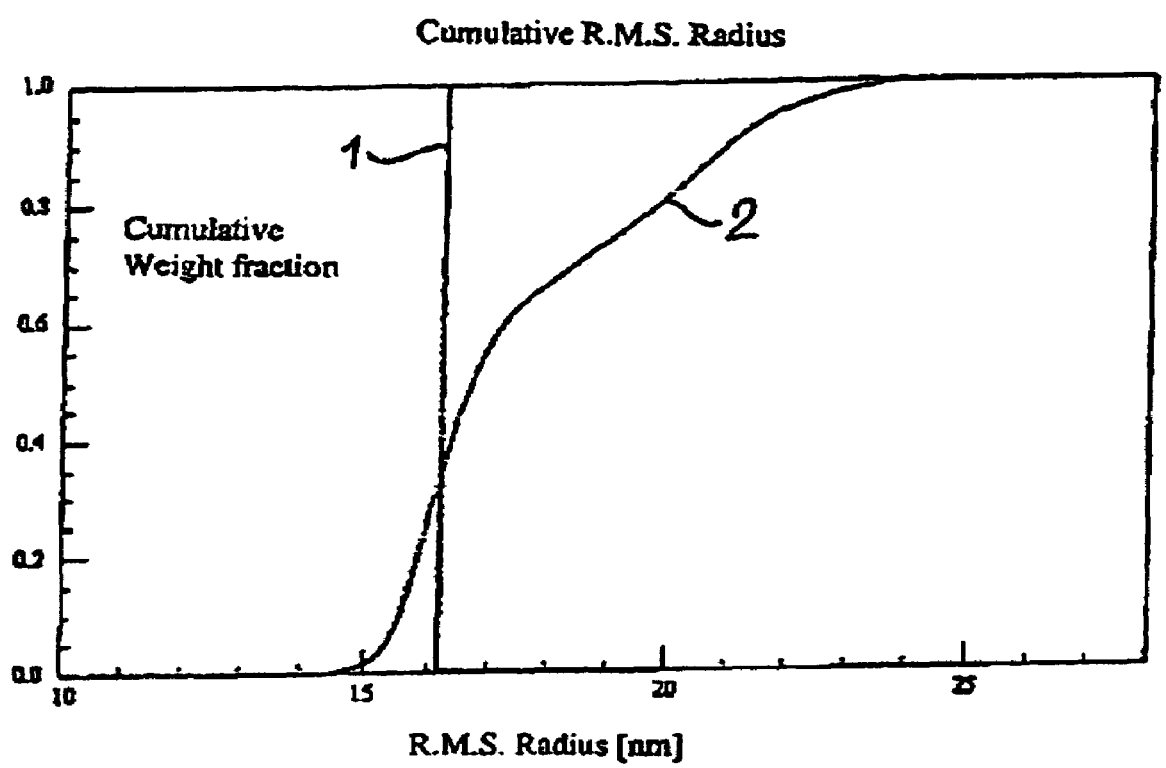
FIG. 1 is a graph of the R.M.S. radius of a sample of the 4% isoflavone concentrate in Example 2 after dilution in water at a ratio of 1:200. The resulting 0.02% isoflavone concentrate dilution is submitted to the field/flow fractionation with a downstream DAWN-EOS detector from Wyatt technology. Curve 1 shows an R.M.S. radius of the isoflavone concentrate in Example 2 of about 16 nm, and Curve 2 is a reference curve.

The invention is therefore based on the task of increasing the bio-availability and resorption of the mentioned agents on one hand, and of easing the incorporation of these agents into the end products in the food, cosmetics, and pharmaceutical industries on the other hand.

For this purpose, the invention provides an isoflavone concentrate that contains a polysorbate, as well as one or more of the agents genistein, daidcein, glycitein, and/or their glycosides. The concentrate according to the invention is soluble in water as a clear solution. When this solution is administered, the isoflavones of the type genistein are slightly resorbed in the gastrointestinal tract. It is therefore possible to add a dosage of the concentrate according to the invention to alcohol-free beverage with the result that the general isoflavone absorption of the organism is quasi casually and simultaneously increased with the consumption of beverages. Isoflavones of the type genisetin in the form of a water soluble concentrate can be used in the classical food industry, and advantageously in the cosmetics or skin care industries. The water solubility ensures a substantially higher absorption of the isoflavones through the skin.

Agents of a purely vegetable origin are preferred. It is recommended for an agent concentrate containing isoflavone, to generally use a powder processed soybean extract, which contains 400 g of a mixture of genistin, daidcin, and glycitin, as well as their aglycons per kilogram. Advantageously, the quantity ratio of genistin, daidcin, and glycitin would then be about 1.3:1.0:0.3.

Preferably, polysorbate 80 is used for the production of the concentrate according to the invention. For the use according to the purpose of the invention, polysorbate 20, polysorbate 40, polysorbate 60, and polysorbate 65 are also suitable, which are obtained from sorbitol as the partial ester of lauric, palmitic, or stearic acid.

In addition to non-alcoholic beverages, the object of the invention therefore also includes liqueurs, various foods, and also skin care products, cosmetics, and such products that contain an isoflavone concentrate of polysorbate, and one or more of the agents genistein, daidcein, glycitein, and/or their glycosides. Purposefully, a beverage, for instance, contains approximately 0.5 g to approximately 3 g of isoflavone concentrate per liter. This water-free concentrate can be packaged undiluted into gelatin and/or gelatin-free capsules as antioxidants, or dietary supplements.

For the production of a water-soluble concentrate containing isoflavones, for instance, 100 g of soybean extract powder is used as the base product, which is distributed by Archer-Daniels-Midland Company, USA under the brand name NOVASOY. This soybean extract contains at least 40 wt-% of genistin, daidcin, and glycitin, and their aglycons at a quantity ratio of 1.3:1.0:0.3. 100 g of the said extract therefore contain 20.0 g of genistin, 15.4 g of daidcin, and 4.6 g of glycitin, a total of 40.0 g of isoflavones.

For example, the said powdered soy extract with the brand name NOVASOY, distributed by Archer-Daniels-Midland Company, Decatur, Ill., USA, serves for the production of a water-free isoflavone concentrate containing isoflavones, which mainly contains the glycosides of genistein, daidcein, and glycitein.

EXAMPLE 1

Approximately 166 g of this soy extract powder is trickled into approximately 834 g of polysorbate that has been heated to approximately 750° Celsius, and the mixture (1.0 kg) is consistently stirred for about half an hour at this temperature. A deep brown, clear concentrate without sediment is the result. If about 1–2 ml of this concentrate is added to ten times the amount of distilled water, a clear solution is obtained after completion of the mixing process.

1.0 kg of this concentrate contains approximately 66 g of isoflavone. By adding 1.5 g of the concentrate to 1.0 liters of a finished beverage, this beverage then contains about 100 mg of the said isoflavone so that one liter of a finished beverage processed in this way sufficiently covers the daily requirement of isoflavone.

Instead of NOVASOY, soy extracts of other sources can also be used, which are distinguished by their substantial lack of sugar. For instance, K.-W. Pfannenschmidt GmbH, Hamburg, supplies a soybean extract that has a total isoflavone content of at least 40%. This approximately 40% is comprised of 7.58% of genistin, 25.43% of genistein, 5.48% of daidcin, and 1.67% of daidcein. Approximately the same results are achieved, if this soybean extract is processes as described in connection with NOVASOY.

The preceding describes the production of a water-free agent concentrate. However, it is also possible to achieve a watery agent concentrate according to the following examples:

The extraction of the watery isoflavone concentrate according to the invention provides that the named compounds are trickled into water that has been heated to approximately 60° C., and the mixture is stirred at the said temperature during a predetermined time period of about ten minutes. Polysorbate is then added to the mixture, and the temperature is increased to about 100° C. The stirring process is continued at this temperature until the mixture has turned clear and transparent. Alternatively, polysorbate can first be added to the compounds, and then the water can be added.

EXAMPLE 2

For example 100 g of the mentioned soybean extract NOVASOY is evenly stirred into 400 g of distilled water that has previously been heated to approximately 60° C. the mixture (total quantity 500 g) is consistently stirred using a magnetic stirrer while maintaining the temperature of about 60° C. for about ten minutes. While continuing the stirring process, 500 g of polysorbate 80 is added, and the temperature is increased to approximately 100° C.

The stirring process is continued at this temperature until the mixture (total quantity 1 kg) has turned clear and transparent. This clear mixture contains the incorporated 40 g of isoflavone.

If a water-soluble isoflavone concentrate is desired to contain less water specifically to the end product, the water quantity to be added according to the following example 3 can be compensated, or reduced partially by adding triglycerides, or a light vegetable oil (such as safflower oil). The weight ratio of NOVASOY to polysorbate 80 should be selected at about 1:6 in this case, while it is about 1:5 in the previous examples.

EXAMPLE 3

100 g of the mentioned soybean extract NOVASOY is evenly stirred into 230 g of distilled water that has been heated to about 60° C. The mixture (total quantity 330 g) is consistently stirred with a magnetic stirrer while maintaining the temperature at about 60° C. for approximately five minutes. While the stirring process is continued, and the temperature is maintained, about 70 g of vegetable oil (safflower oil) is added, and stirred for approximately five minutes. Subsequently, 600 g of polysorbate 80 is added to the mixture (400 g), and the temperature is increased to approximately 100° C. The stirring process is continued at this temperature until the mixture (total quantity 1 kg) has turned transparent, or results in a clear, brownish solution dissolved in water. This clear mixture contains the incorporated 40 g of isoflavone.

2.5 g of this clear, stable watery concentrate contain 100 mg of isoflavone. This quantity, for instance, can be incorporated into one liter of a finished beverage, which thereby covers twice the daily requirement of an amount of 50 g of isoflavone.

Instead of safflower oil, sunflower oil, linseed oil, soy oil, or olive oil can also be used. All of these oils distinguish themselves by a high content of triglycerides, such as α-linolenic acid, γ-linolenic acid, linoleic acid, or oleic acid. For example, safflower oil contains up to 83% of linoleic acid, and up to 24% of oleic acid; linseed oil contains up to 71% of linolenic acid, up to 31% of linoleic acid, and up to 23% of oleic acid. Therefore, one or more triglyceride-rich oils, preferably of vegetable origin, may be used instead of safflower oil.

In order to accelerate and optimize the mixing process and the solubility, it is recommended to heat the isoflavone concentrates according to examples 1 to 3 to approximately 70° C. before the mixing process, and the water, in which the concentrate is to be dissolved, to approximately 40° C., also before the mixing process.

The stability of the concentrate according to the invention in its clarity and water solubility is given also if gastric acid is added to the concentrate according to the invention, or to a preparation produced from it (i.e. a beverage). This is true also if the concentrate is heated, for instance, to about 100° C. The concentrate also distinguishes itself by an excellent stability.

Micelles are present in the isoflavone concentrates according to the invention, the interiors of which contain isoflavones, which are surrounded by polysorbate molecules. The median radius of the micelles is below 20 nm. As a verification, the 4% isoflavone concentrate resulting in example 2 is diluted in water at a ratio of 1:200, and the 0.02% isoflavone concentrate dilution achieved in this way is submitted to the field/flow fractionation with a downstream DAWN-EOS detector according to Wyatt technology. The result is reflected in FIG. 1, which shows curve 1 with a R.M.S. radius of the sample of about 16 nm, and where curve 2 is a reference curve.

The invention claimed is:

1. A method for the production of an isoflavonoid concentrate mixture which comprises:
    a) heating a polysorbate heated to the range of about 60° C. to about 100° C.;
    b) adding the heated polysorbate of step a) to an extract containing tile an isoflavonoid mixture containing genistein, daidzein glycitein, and their glycosides; and
    c) stirring the warm mixture of step b) evenly until a clear, sediment-free and water soluble concentrate is produced.

2. The method according to claim 1, wherein the extract is initially introduced into water heated to about 60° C., then the polysorbate is added and the temperature is raised to about 100° C.

3. The method according to claim 1, wherein polysorbate 80 is used.

4. The method according to claim 2, wherein polysorbate 80 is used.

5. The method according to claim 1 wherein approximately 166 weight units of soybean extract powder are introduced into about 834 weight units of polysorbate at about 75° C. and the mixture is until obtaining a clear concentrate without sediment.

6. The method according to claim 4, wherein about 100 weight units of soybean extract are stirred into about 400 weight units of water of about 60° C., after continued stirring about 70 weight units of a vegetable oil and thereafter about 500 weight units of polysorbate 80 are added.

7. The method according to claim 4 wherein about 100 weight units of soybean extract are stirred into about 230 weight units of water of about 60° C., after continued stirring about 70 weight units of vegetable oil and thereafter about 600 weight units of polysorbate 80 are added.

8. The method according to claim 3, wherein the weight ration of the extract to polysorbate 80 is approximately 1:5.

9. The method according to claim 4, wherein the weight ratio of the extract to polysorbate 80 is approximately 1:5.

10. The method according to claim 1, wherein a light triglyceride-rich oil, including safflower oil or sunflower oil, is added to the extract.

11. The method according to claim 7, wherein up to approximately 7% by weight of safflower oil is added.

12. The method according to claim 1, wherein genistein, daidzein, and glyceitin are present in the extract in a ratio of 1.3:1.0:0.3.

13. The method of claim 10, wherein said light triglyceride-rich oil is of plant origin.

14. The method for the production of an isoflavonoid concentrate mixture of claim 1 wherein the mixture is of plant origin.

* * * * *